US012605170B2

(12) United States Patent
Naylor et al.

(10) Patent No.: US 12,605,170 B2
(45) Date of Patent: Apr. 21, 2026

(54) FEMORAL HEAD RESTORATION

(71) Applicant: DEPUY IRELAND UNLIMITED COMPANY, County Cork (IE)

(72) Inventors: Jason Naylor, Leeds (GB); Caroline Wither, Leeds (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 540 days.

(21) Appl. No.: 17/996,834

(22) PCT Filed: Apr. 27, 2021

(86) PCT No.: PCT/EP2021/060994
§ 371 (c)(1),
(2) Date: Oct. 21, 2022

(87) PCT Pub. No.: WO2021/219642
PCT Pub. Date: Nov. 4, 2021

(65) Prior Publication Data
US 2023/0165595 A1 Jun. 1, 2023

(30) Foreign Application Priority Data

Apr. 27, 2020 (GB) .................................... 2006158

(51) Int. Cl.
*A61B 17/17* (2006.01)
*A61B 17/16* (2006.01)
(Continued)

(52) U.S. Cl.
CPC .......... *A61B 17/175* (2013.01); *A61B 17/164* (2013.01); *A61F 2/4657* (2013.01);
(Continued)

(58) Field of Classification Search
CPC ...... A61B 17/175; A61F 2/4657; A61F 2/468; A61F 2/4684; A61F 2002/4658; A61F 2002/4687
See application file for complete search history.

(56) References Cited

U.S. PATENT DOCUMENTS

| 4,959,066 A | * | 9/1990 | Dunn | ..................... | A61B 17/15 |
| | | | | | 606/89 |
| 5,342,366 A | * | 8/1994 | Whiteside | .............. | A61B 90/06 |
| | | | | | 606/86 R |

(Continued)

FOREIGN PATENT DOCUMENTS

| DE | 10322760 A1 | 12/2004 |
| EP | 1430859 A1 | 6/2004 |

(Continued)

OTHER PUBLICATIONS

Great Britain Search Report received for GB Application No. 2006158.6, mailed on Oct. 14, 2020, 1 page.
(Continued)

*Primary Examiner* — Nicholas W Woodall
(74) *Attorney, Agent, or Firm* — Barnes & Thornburg LLP

(57) ABSTRACT

A surgical instrument and method for assessing restoration of the femoral head centre is provided. The instrument comprising: a body having a first connector for attaching the body to a femoral part, and wherein the body defines a plurality of apertures therein, wherein each aperture corresponds to a respective femoral head centre arising from a respective corresponding femoral neck; and a gauge, wherein the gauge includes a pin at a first end and an arm extending transversely from the pin and wherein the pin is receivable in each of the plurality of apertures and the arm bears a scale indicating a distance from the pin. The approach seeks to provide a simple and/or easy to use
(Continued)

approach to restoring the native femoral head position during a hip replacement surgical procedure.

12 Claims, 5 Drawing Sheets

(51) Int. Cl.
*A61F 2/46* (2006.01)
*A61B 90/00* (2016.01)

(52) U.S. Cl.
CPC ................. *A61B 2090/0811* (2016.02); *A61B 2090/3916* (2016.02)

(56) References Cited

U.S. PATENT DOCUMENTS

| | | | | |
|---|---|---|---|---|
| 5,792,143 | A * | 8/1998 | Samuelson | A61F 2/4607 606/102 |
| 6,258,097 | B1 | 7/2001 | Cook et al. | |
| 10,980,646 | B2 * | 4/2021 | Grobler | G01B 3/20 |
| 11,490,901 | B2 * | 11/2022 | Atkin | A61B 17/155 |
| 11,590,004 | B2 * | 2/2023 | Awais | A61F 2/4607 |
| 11,642,137 | B2 * | 5/2023 | Mulqueen | A61B 17/1668 606/89 |
| 11,992,226 | B2 * | 5/2024 | Beverland | A61B 17/15 |
| 2011/0275958 | A1 * | 11/2011 | Barrett | A61F 2/4657 600/595 |
| 2014/0276866 | A1 * | 9/2014 | Endsley | A61F 2/4657 606/89 |
| 2017/0020686 | A1 * | 1/2017 | Baird | A61F 2/4657 |

FOREIGN PATENT DOCUMENTS

| | | | |
|---|---|---|---|
| FR | 2770128 | A1 | 4/1999 |
| FR | 3027215 | A1 | 4/2016 |
| FR | 3028170 | A1 | 5/2016 |
| WO | 2020001830 | A1 | 1/2020 |
| WO | 2020002198 | A1 | 1/2020 |
| WO | WO 2020002190 | A1 | 1/2020 |

OTHER PUBLICATIONS

International Search Report and Written Opinion received for PCT Application No. PCT/EP2021/060994, mailed on Jul. 5, 2021, 14 pages.

Japanese Notice of Reasons for Refusal for Corresponding Patent Application No. 2022-565631, Date of Drafting Nov. 8, 2024, 4 Pages.

* cited by examiner

Figure 7
Figure 6
Figure 5
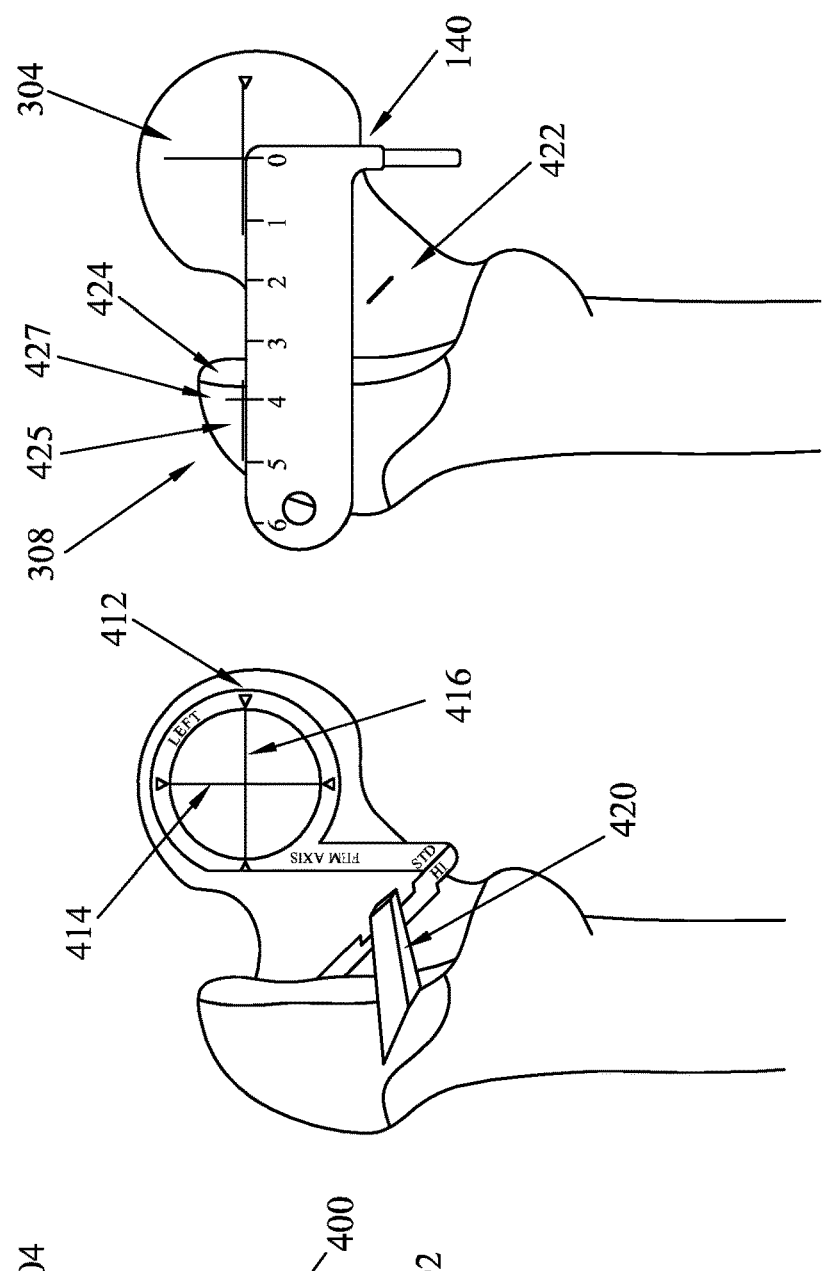
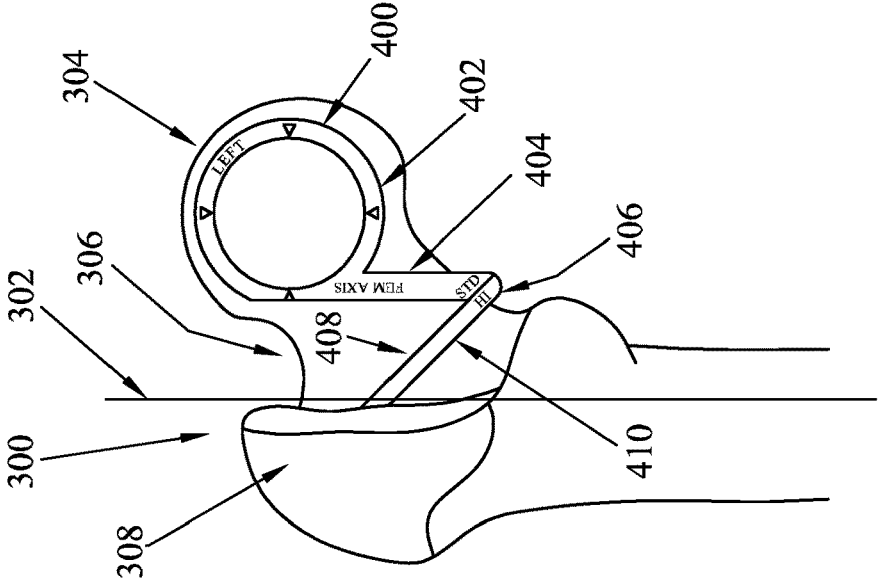

FEMORAL HEAD RESTORATION

CROSS REFERENCE TO RELATED PCT APPLICATION

This application is a National Stage 35 U.S.C. 371 of International Patent Application PCT/EP2021/060994 filed Apr. 27, 2021, which claims priority to United Kingdom Application No. GB2006158.6, filed Apr. 27, 2020, which are both incorporated by reference in their entireties.

The present disclosure relates to surgical instruments and methods, and in particular to surgical instruments and methods for use in restoring the femoral head centre in a hip replacement procedure.

A variety of different hip replacement procedures are known generally. Some of these involve removing the native femoral head and replacing it with a prosthetic femoral head. Often a stem is used including a prosthetic femoral neck to which the prosthetic femoral head is attached. Sometimes an acetabular cup may also be used to replace the native acetabulum of the patients pelvis. The specific details may vary depending on the implant system being used.

The positioning of the prosthetic components can be an important factor in the outcome of the hip replacement procedure. A variety of different philosophies or approaches to implant placement exist and may vary depending on the implant system and/or the individual circumstances of the patient.

One approach is a restorative approach in which the surgeon tries to replicate or restore the native anatomy of the patient prior to the hip replacement procedure.

For example, pre-operative images, such as X-ray images or CT scans, may be used to determine the anatomy of the patients femur and then used to plan the prosthetic implant components and their positioning so as to attempt to restore the patients native anatomy. However, such approaches require the availability of imaging apparatus, may take more time, may be more complicated, and may require greater surgeon experience or skill.

Therefore, simpler approaches to helping to restore native anatomy would be beneficial.

The present disclosure is directed to surgical instruments, apparatus, kits of parts and methods which may provide a simple and/or easy to use approach to restoring the native femoral head position during a hip replacement surgical procedure.

A first aspect of the present disclosure provides a surgical instrument for assessing restoration of the femoral head centre, comprising: a body having a first connector for attaching the body to a femoral part, and wherein the body defines a plurality of apertures therein, wherein each aperture corresponds to a respective femoral head centre arising from a respective corresponding femoral neck; and a gauge, wherein the gauge includes a pin at a first end and an arm extending transversely from the pin and wherein the pin is receivable in each of the plurality of apertures and the arm bears a scale indicating a distance from the pin.

The plurality of apertures may include apertures corresponding to femoral necks having different medial-lateral offsets.

The plurality of apertures may include apertures corresponding to femoral necks having different stem-neck angles.

The plurality of apertures may include apertures corresponding to femoral necks having different leg-lengths.

The body may have an anterior face and the anterior face may include at least a first linear indicium extending parallel to a medial-lateral axis and passing through at least a first of the plurality of apertures and corresponding to a first position on a superior-inferior axis.

The anterior face may include at least a second linear indicium extending parallel to the medial-lateral axis and passing through at least a second of the plurality of apertures and corresponding to a second position on the superior-inferior axis.

The body may have a posterior face and the posterior face may include the same indicia as the anterior face and may be configured so that the same body is useable for right hand hips and left hand hips.

The body may have a posterior face and the posterior face may define a posterior plane and the anterior face may define an anterior plane and the anterior plane may be parallel to the posteriori plane.

Each of the plurality of apertures may comprise a channel passing through the entire thickness of the body. Each channel may pass from the anterior face through the body to a or the posterior face.

A second aspect of the disclosure provides a surgical instrument system comprising: the surgical instrument of the first aspect; and a centre finder. The centre finder may include a plurality of indicia configured to indicate the centre of the centre finder.

The centre finder may comprise a circular ring. The plurality of indicia may comprise a first pair of diametrically opposed indicia and/or a second pair of diametrically opposed indicia.

The surgical instrument system may further comprise a broach. The broach may include a second connector configured to engage the first connector to attach the body to the broach.

The surgical instrument system may further comprise a plurality of femoral necks. Each neck may give rise to a different femoral head centre position.

The plurality of femoral necks may include femoral necks having different offsets along the medial-lateral axis.

The plurality of femoral necks may include femoral necks having different stem-neck angles.

The plurality of femoral necks may include femoral necks having different leg lengths along the superior-inferior axis.

The femoral necks may be trial necks or prosthetic necks.

A third aspect of the disclosure provides a method for assessing restoration of the femoral head centre for a femur of a patient. The method may include one or more of: determining the centre of the native femoral head of the femur of the patient; marking the position of the centre of the native femoral head on the native femoral head; marking a position on the greater trochanter of the femur relative to the centre of the native femoral head with a known separation along the medial-lateral axis from the centre of the native femoral head and at the same position along the superior-inferior axis as the centre of the native femoral head; resecting the native femoral neck; attaching a body to the resected femoral neck, wherein the body defines a plurality of apertures, each aperture corresponding to a respective femoral head centre arising from a respective corresponding femoral neck; attaching a gauge including a scale to the body using a first one of the plurality of apertures; and using the gauge to determine whether the femoral head centre arising from a first femoral neck corresponding to said first one of the plurality of apertures would restore the native femoral head centre.

The method may further comprise; attaching the gauge to the body using a second one of the plurality of apertures; and using the gauge to determine whether the femoral head centre arising from a second femoral neck corresponding to said second one of the plurality of apertures would restore the native femoral head centre.

The method may further comprise: aligning the gauge with a linear indicium on the body which is parallel to the medial-lateral axis of the femur.

The method may further comprise; using the scale on the gauge to determine whether the femoral head centre arising from the femoral neck corresponding to said one of the plurality of apertures would have a separation restoring the known separation.

The method may further comprise: using a centre finding guide placed on the native femoral head to determine the centre of the native femoral head and/or to mark the position of the centre of the native femoral head An embodiment will now be described in detail, by way of example only, and with reference to the accompanying drawings, in which:

FIG. 5 shows an anterior view of a proximal part of a native femur and a guide;

FIG. 6 shows the guide being used to mark a femoral resection height;

FIG. 7 shows the guide being used to mark the greater trochanter relative to the centre of the native femoral head;

In the Figures of drawings, like items in the different Figures share common reference signs unless indicated otherwise.

Figures 1, 2:
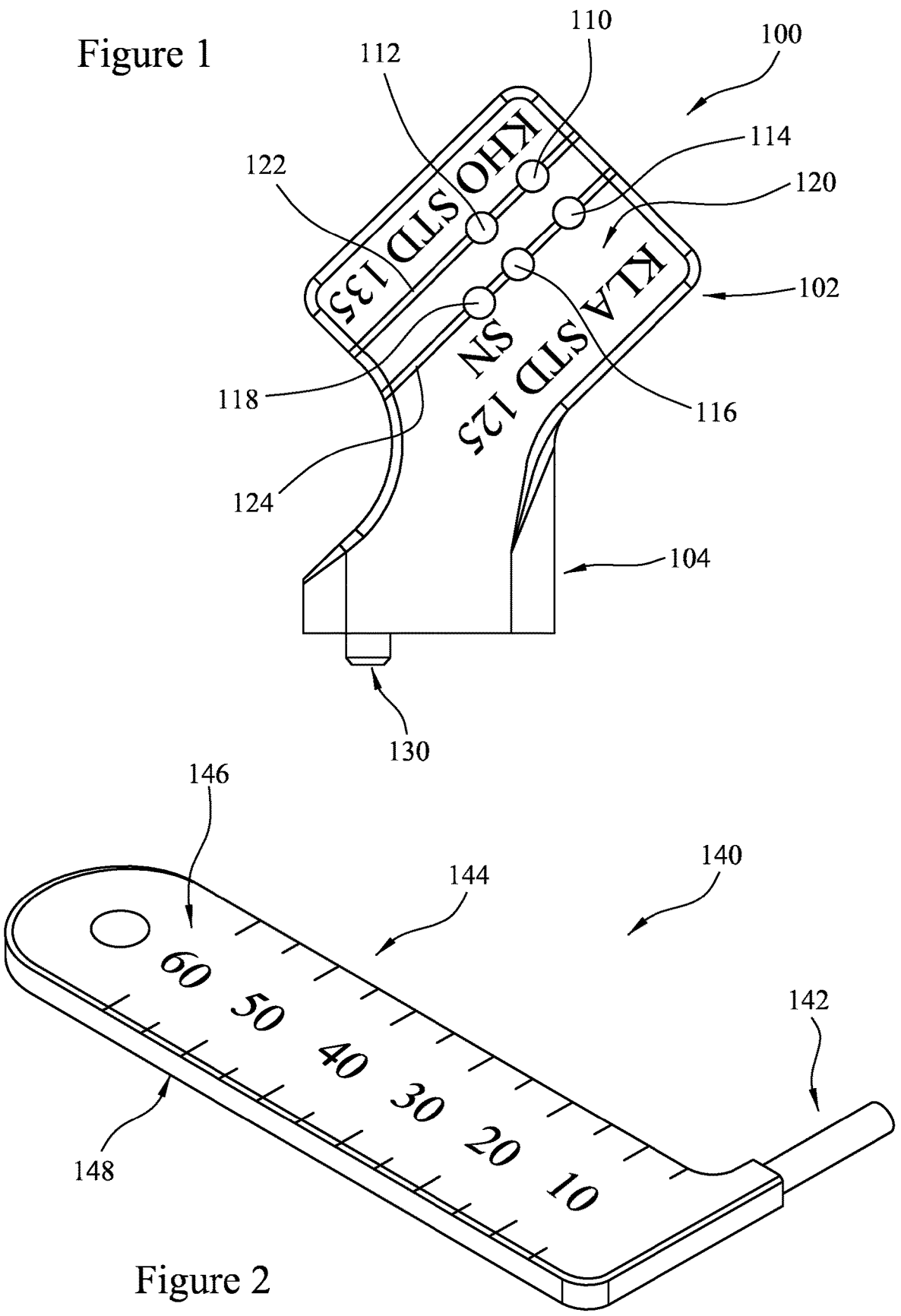
FIG. 1 shows a side elevation of a body part of a head centre restoration instrument.
FIG. 2 shows a perspective view of a gauge part of the head centre restoration instrument.

With reference to FIG. 1 there is shown a side elevation of a first part 100 of a head centre restoration instrument. The first part of the instrument 100 provides a body of the head centre restoration instrument. The body includes a main portion 102 and a connection portion 104 by which the body 100 may be attached to a femoral part in use as described in greater detail below.

The main part 102 of the body 100 defines a plurality of apertures therein. In the illustrated embodiment, five apertures 110, 112, 114, 116, 118 are defined by the body. Each of the apertures passes entirely through the entire width of the main part of the body 102 also has to have an opening on either side of the body. It will be appreciated that five apertures is simply an example, and in other embodiments, a greater or lesser number of apertures may be provided. As described in greater detail below, the position of each aperture corresponds to a corresponding femoral neck, and in particular, to the centre of a femoral component when mounted on the corresponding neck. Hence, in the illustrated embodiment, as there are five apertures, there are also five femoral necks. Each femoral neck has a geometry corresponding to a slightly different position of the centre of the femoral component when mounted on the respective necks.

The femoral necks may have differing stem-neck angles, e.g. 125° or 135°, and/or differing medial-lateral offsets and/or differing leg lengths.

For example, the fourth aperture 116 may correspond to a fourth femoral neck which may be considered a standard or reference femoral neck. The standard femoral neck may have a stem-neck angle of 125° and give rise to a femoral component centre at a standard position in terms of medial-lateral offset and leg length. The standard femoral leg may be referred to as providing a low femoral head position.

The third aperture 114 may be associated with a third femoral neck also having a stem-neck angle of 125°. However, the femoral neck gives rise to a centre of the femoral component giving rise to a lateral offset of the femur relative to the pelvis. For example, the amount of the increased lateral offset may be approximately 7 mm.

The fifth aperture 118 may correspond to a fifth femoral neck again having a neck-stem angle of 125°. However, the femoral neck gives rise to a centre of the femoral component having a reduced distance in the medial-lateral direction and corresponding to a medial offset of the femur relative to the pelvis. The amount of the medial offset may be approximately 5 mm, for example.

The second aperture 112 may correspond to a second femoral neck having a stem-neck angle of 135°. The second femoral neck may give rise to the same medial-lateral position as the standard femoral neck, but give rise to a centre of a femoral head giving rise to an increased leg length in the inferior-superior direction. For example, the amount of the increase in leg length may be approximately 5 mm.

The first aperture 110 may correspond to a first femoral neck also having a neck-stem angle of 135°. The first femoral neck gives rise to a femoral head centre having an increased leg length, relative to the standard neck, and also an increased lateral offset relative to the standard neck. The amount of the increase in leg length may be approximately 5 mm and similarly the amount of the lateral offset may be approximately 7 mm.

The first and second femoral necks may be referred to as "high" femoral necks, and the third, fourth and fifth femoral necks may be referred to as "low" femoral necks.

As indicated in FIG. 1, various indicia and markings may be provided on an anterior surface 120 of the main body part 102 indicating to the user the femoral neck associated with each of the respective apertures. Similar markings may also be provided on the posterior surface of the main body as illustrated in FIG. 1, and which posteriori surface is generally parallel to the anterior surface. Hence, the same body may be used for right hand hips and left hand hips, or for anterior or posterior approaches, as it is essentially symmetric about the central plane parallel to the anterior and posterior surfaces of the body.

As also illustrated in FIG. 1, a first linear indicium 122 and a second linear indicium 124 is also provided on the anterior surface 120. The first linear indicium 122 passes through the first and second apertures and extends generally along the medial-lateral axis of the patients anatomy when the body 100 is mounted on the patients femur in use. Similarly, second linear indicium 124 extends through the third, fourth and fifth apertures and again extends generally parallel to the medial-lateral axis of the patients anatomy when body 100 is mounted on the patients femur in use.

The connecting or foot portion 104 defines a peg 130 and cavity 132 providing first and second attachment features for releasably attaching the body 100 to a femoral component in use. The provision of a peg and cavity helps to ensure that the body 100 is attached correctly to the femoral part in use.

FIG. 2 shows as perspective view of a gauge 140 part of the head centre restoration instrument. The gauge 140 has a pin 142 at a first end. The pin 142 is dimensioned to be snuggly received in any one of the plurality of apertures of the body 100. As illustrated in FIG. 2, the peg has a generally right circular cylindrical form.

The gauge 140 also includes an arm or member 144 extending generally transversely to a longitudinal axis of the pin 142. The arm includes a plurality of indicia on a first 146 surface and also on the reverse surface 148. As illustrated in FIG. 2, the indicia provided on the arm 144 provide a scale indicating a distance or separation between an origin defined by the location of the pin 142 and the transverse distance along the longitudinal axis of the arm 144.

In some embodiments, as illustrated in FIG. 2, the scale may also provide a ruler and include numerals indicating the magnitude of the distance. For example, 10, 20, 30, 40, 50, 60 mm. However, in other embodiments, the gauge may not be in the form of a ruler and may simply include any markings which allow a visual assessment of the distance between a point on the arm 144 and the position of the pin 142.

Figure 3:
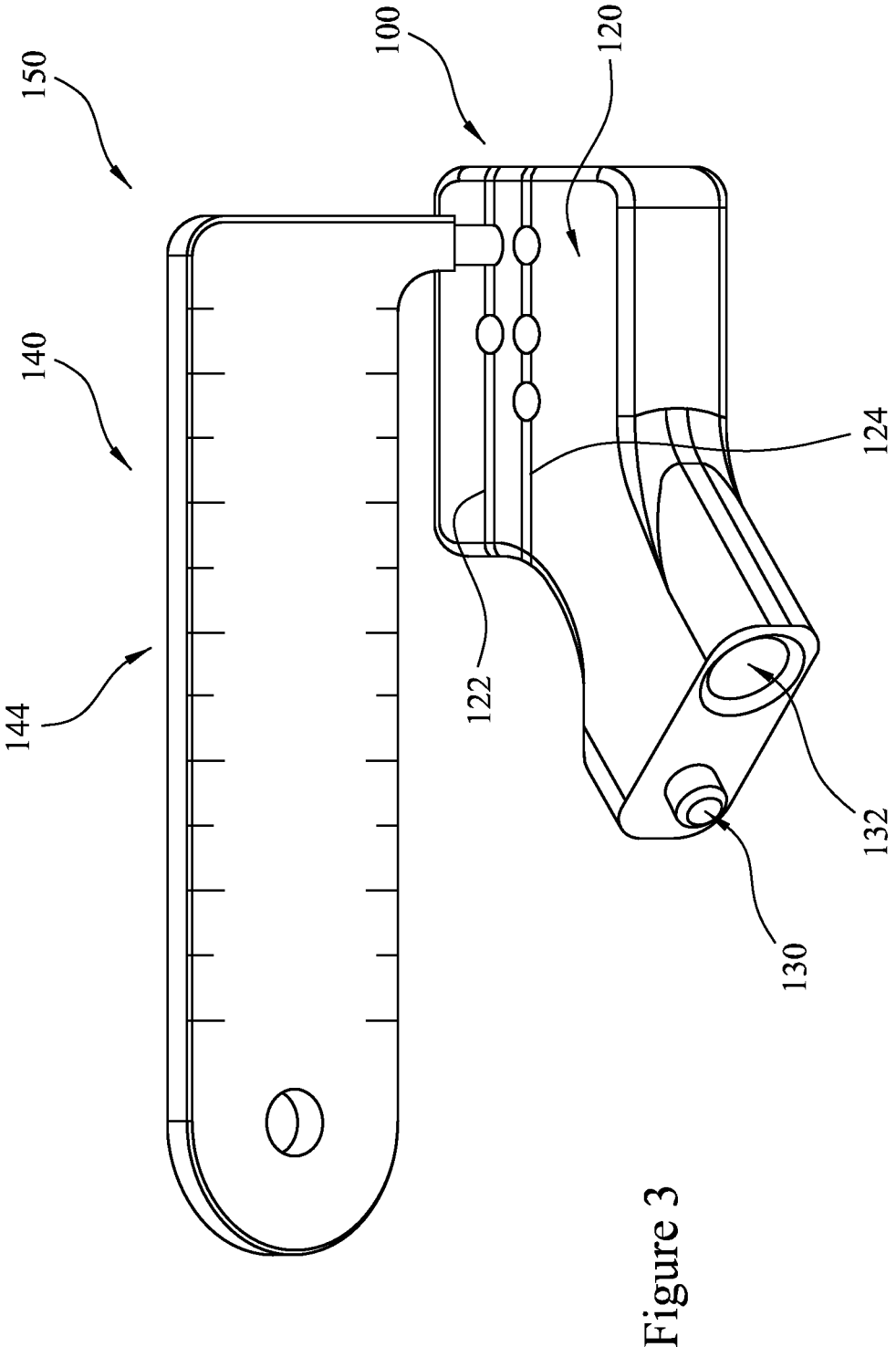
FIG. 3 show a perspective view of the head centre restoration instrument comprising the gauge and body.

FIG. 3 shows a perspective view of the head centre restoration instrument 150 comprising the gauge 140 mounted on the body 100. As illustrated in FIG. 3, the pin 142 is received within the first aperture 110. The longitudinal axis of the pin extends substantially transversely to the plane of the anterior surface 120 of the body. As also illustrated in FIG. 3, the longitudinal axis of the arm 144 is substantially parallel to the first linear indicium 122.

The configuration of the body and gauge illustrated in FIG. 3 corresponds to the relative position of the body and gauge in use, as described in greater detail below.

Figure 4:
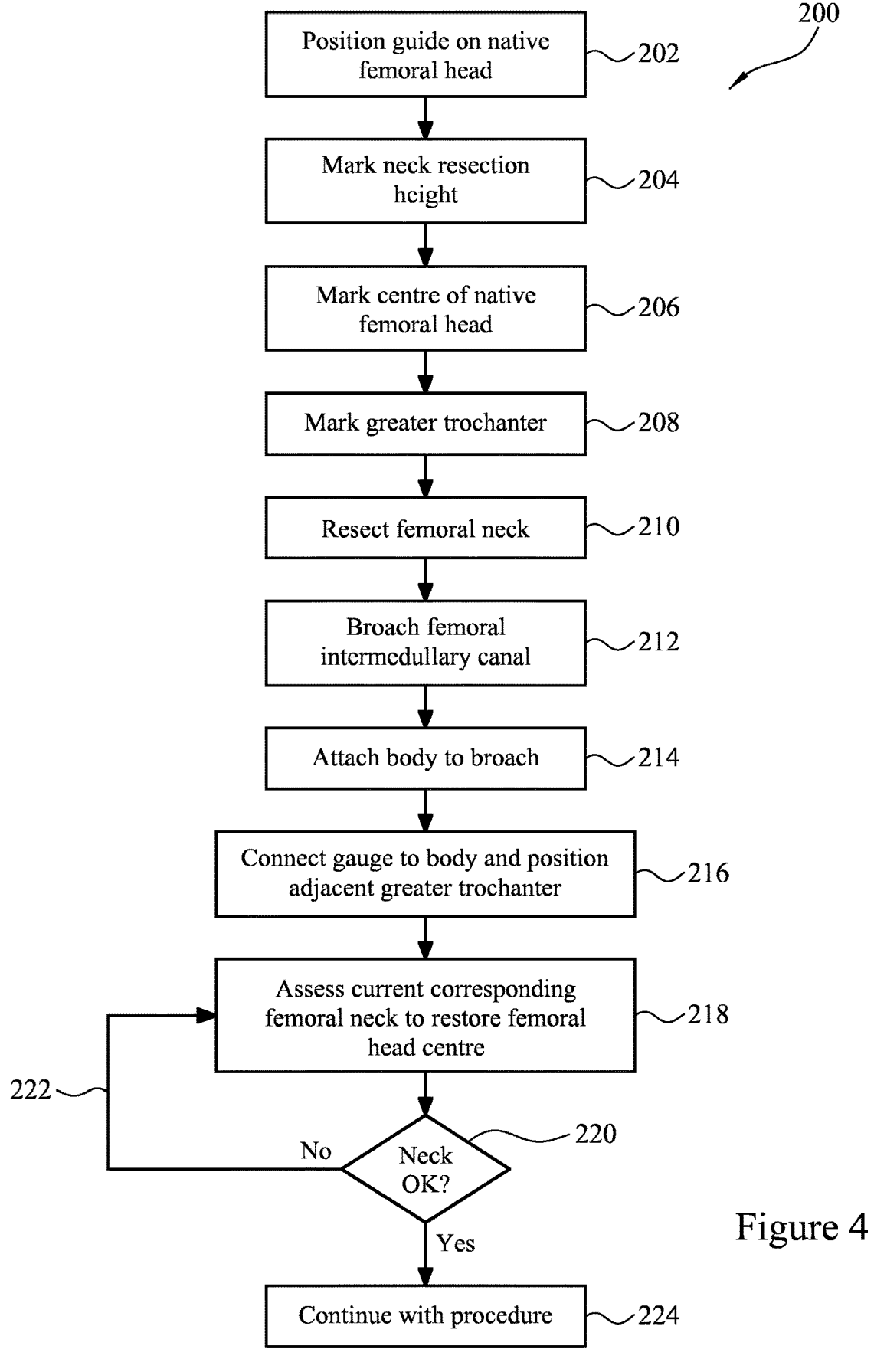
FIG. 4 shows a flow chart illustrating a method for restoring the native femoral head centre using the head centre restoration instrument as part of a hip replacement procedure.

FIG. 4 shows a flow chart illustrating a general method of use of the head centre restoration instrument 150 illustrated in FIG. 3 as part of a hip replacement procedure. Various parts of the hip replacement procedure are generally known to a person of ordinary skill in the art, and therefore are not shown in the flow chart illustrated in FIG. 4. Hence, FIG. 4 shows merely a sub-set of the surgical method so as not to obscure the description of the present invention. The method 200 illustrated in FIG. 4 will now be described in greater detail with further reference to FIGS. 5 to 10.

FIG. 5 shows an anterior-posterior view of the approximal part of a femur 300 of a patient. Line 302 is generally parallel with the anatomical axis of the femur 300. The proximal part of the femur 300 generally comprises the native femoral head 304, the native femoral neck 306 and the native greater trochanter 308.

FIG. 5 also shows a guide component 400 which may optionally be used to improve the overall accuracy of the procedure. The guide component 400 includes a centre finding part 402, a first arm 404 and a second arm 406. The centre finding part 402 generally has a circular annular construction. Hence, as it is in the form of a generally circular ring, when the centre finding part 402 is mounted on the femoral head 304, which is approximately spherical, it will naturally sit with its centre generally aligned with the centre of the native femoral head 304. The first arm 404 is aligned to lie parallel to the anatomical femoral axis 302. The length of the first arm 404 and the angle between the second arm 406 and the first arm 404 is predefined so as to indicate a preferred resection height and angle for resecting the native femoral neck 306. An upper edge 408 of the second arm 406 may be used to define a first resection height (a standard resection height) and a lower edge 410 may be used to define a second resection height (corresponding to a high neck resection).

At 202, the guide 400 is positioned on the native femoral head and oriented so that the first arm 404 is generally parallel to the anatomical axis of a femur 302, as illustrated in FIG. 5. Then, at 204, the second arm 406 may be used to mark a resection height and angle on the native femoral neck as illustrated in FIG. 6. For example, a chisel instrument 420 may be positioned on the femoral neck using the upper edge 408 of the second arm 406 and used to mark the neck resection height and angle on the native femoral neck 306.

The guide 400 is then used at 206 to mark the approximate centre of the native femoral head 304. As illustrated in FIGS. 5 and 6, the annular ring 402 of the guide component 400 includes four indicia, each in the form of an arrow, e.g. 412. A first pair of indicia or markings define a first axis substantially parallel to the axis of the first arm 404, or the inferior-superior axis of the patients femur. A second pair of markings define a second axis substantially perpendicular to the first axis and the longitudinal axis of the first arm 404, and generally parallel to the medial-lateral axis of the patients femur. Hence, the second pair of markings define a second axis generally parallel to the medial-lateral axis of the native femur. Hence, at 206, the surgeon may mark the approximate centre of the native femoral head by drawing a first line 414 between the first pair of markings and a second line 416 between the second pair of markings. As the markings of each pair of markings are diametrically opposed, the intersection of the two lines generally corresponds to the centre of the annular ring 402 and therefore also generally to the approximately centre of the native femoral head 304.

After the centre of the femoral head has been marked, the guide 400 may be removed. FIG. 7 shows the native femur after removal of the guide 400 and shows the marking on the native femoral neck 422 indicating the preferred neck resection height and angle. At 208, a mark is made on a part of the native femur which will remain after resection of the native femoral head. The marking may be made in any suitable part of the remaining femur and as illustrated in FIG. 7 is generally in the region of the greater trochanter. As illustrated in FIG. 7, the marking on the greater trochanter is made at a known distance from the marked centre of the native femoral head. The marking may be made by placing the gauge 140, or a rule, or similar, adjacent the native femoral head 304 and generally aligned with the second line 416 and hence the medial-lateral axis of the native femur. The marking 424 on the greater trochanter 308 includes a first line 425 generally parallel to the medial-lateral axis and a second line 427, perpendicular thereto, clearly indicating the separation between the marking 424 on the greater trochanter 308 and the centre of the native femoral head 304. The distance along the medial-lateral axis is arbitrary and the position of the vertical marking 427 may be determined more by which part of the greater trochanter is more accessible. The position of the vertical marking 427 does not need to correspond to any particular value of distance. It is simply that the vertical marking provides a fixed separation to the centre of the native femoral head and which distance is known. For example, as illustrated in FIG. 7, the distance between the centre of the native femoral head and the marking 424 is approximately 4 cm.

After the greater trochanter has been marked, at 210, the femoral neck may be resected using the neck resection marking 422 to achieve the desired neck resection height and angle. The intramedullary canal of the femur may then be formed as generally known in the art. Forming the intramedullary canal may involve using various cutting instruments such as rasps and broaches. Eventually, a final broach may be used once the cavity has the size desired for the intended prosthetic implant.

Figures 8, 9, 10:
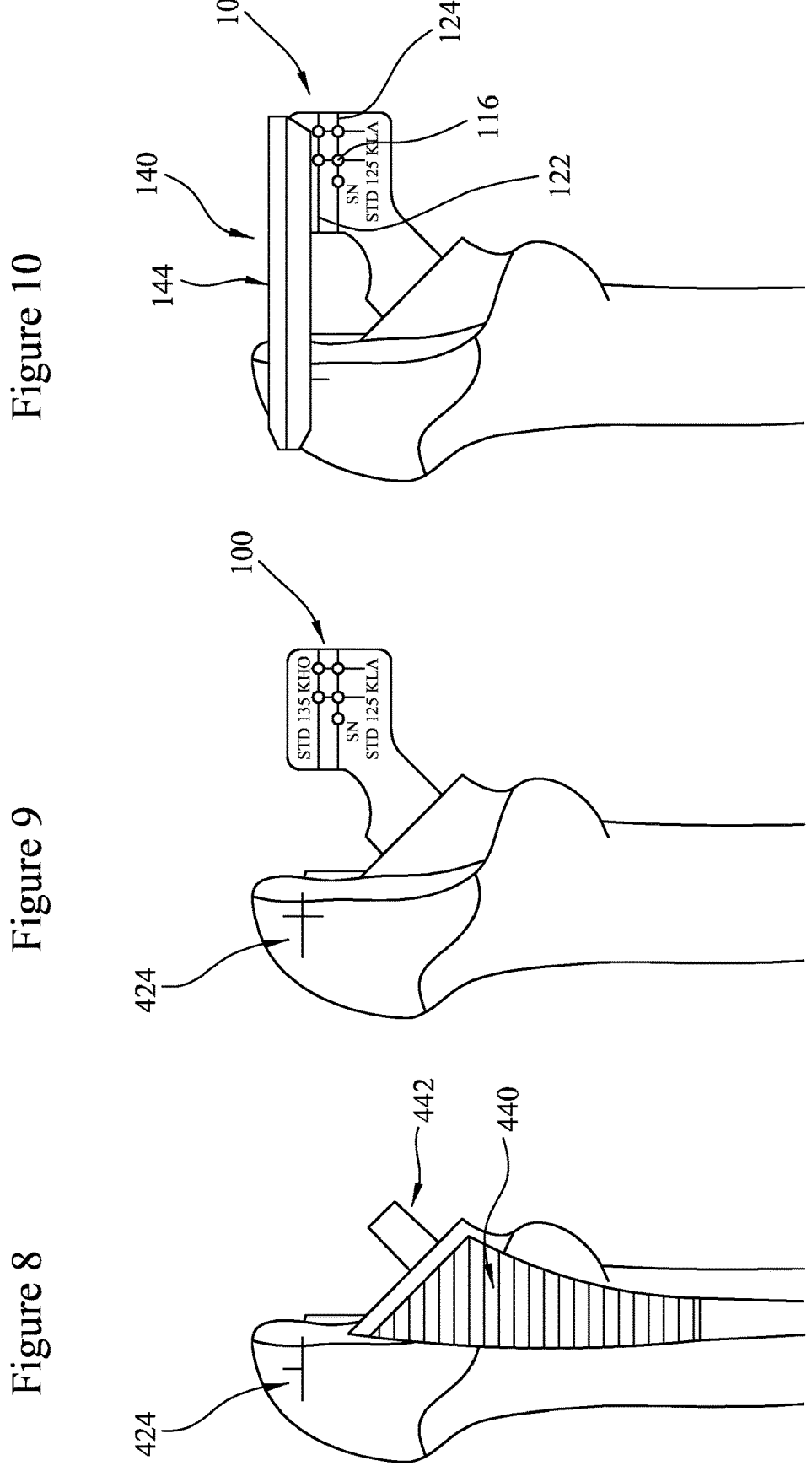
FIG. 8 shows a broach in the femur after neck resection.
FIG. 9 shows the body part of the head centre restoration instrument mounted on the broach.
FIG. 10 shows the gauge part being used with the body of the head centre restoration instrument to assess which trial neck to use to restore the centre of the femoral head.

FIG. 8 illustrates the femur and shows the marking 424 on the remaining part of the native femur and also a final broach 440 located within the intramedullary canal. As illustrated in FIG. 8, the final broach 440 includes a male attachment formation 442 extending therefrom and also includes a female attachment formation (not visible) positioned and configured to mate with male attachment formation 130 on the body 100. In other embodiments the attachment formations on the broach and on the body can be swapped. For example is a female broach were used instead, then a male attachment formation would be provided on the body to engage therewith.

At 214, the body 100 is mounted on the broach 440 as illustrated in FIG. 9. If desired, the marking 424 may have the vertical line extended, generally parallel to the anatomical femoral axis, as illustrated in FIG. 9. Then at 216, the gauge 140 may be attached to the body 100 by inserting the pin 142 in a respective one of the apertures 110 to 118, each corresponding to a different femoral neck. As illustrated in FIG. 10, the pin 142 has been inserted in the first aperture 110 and hence corresponds to a femoral neck with a stem neck angle of 135° and being a high neck compared to a standard neck. The arm 144 is aligned with the first linear indicium 122 so as to be generally parallel to the medial-lateral axis. As illustrated in FIG. 10, the arm 144 of the gauge generally overlies the horizontal line of marking 424. Hence, this indicates to the user that the femoral neck corresponding to the currently used aperture would give rise to a femoral head centre substantially reproducing the position of the centre of the native femoral head in the inferior-superior direction.

Hence, at 218, the surgeon uses the gauge 140 to assess which of the apertures in the body 100 may most closely position a prosthetic femoral head closest to the centre of the native femoral head so as to restore the native femoral head. At 218 the surgeon may look at the scale on the gauge 140 to assess the position in the medial-lateral direction. For example, if the scale on the arm 144 indicates that the separation in medial-lateral direction would be approximately 5 cm, then the surgeon may determine at 220 that the femoral neck corresponding to the first aperture may not be appropriate as previously the preferred separation between the centre of the femoral head and the marking on the trochanter has been determined to be approximately 4 cm. Hence, at 220, if the surgeon determines that a femoral neck corresponding to the currently used aperture may not be appropriate, then the method returns, as illustrated by process flow line 222 to step 218. At 218, the surgeon may remove the gauge 140 from the body 100 and engage the pin 142 in another one of the plurality of apertures. For example, if the surgeon positions the gauge with the pin 142 in the second aperture 112, then this will reduce the medial-lateral offset of a femoral head placed on the corresponding femoral neck. As discussed above, the second aperture 112 may correspond to a femoral neck giving rise to a reduced separation in the medial-lateral direction of approximately 7 mm. Hence, the surgeon may position the gauge 140 aligned with the first linear indicium 122, and determined using the scale on the gauge that the resulting separation would be approximately 4.3 cm. This may then be considered to be acceptable at 220 as the originally determined ideal separation to restore the native femoral head was determined to be approximately 4 cm. Hence, at step 220, an acceptable femoral neck has been identified, approximately restoring the centre of the native femoral head, and therefore the remainder of the neck replacement procedure may be continued with at 224.

Additionally or alternatively, at 220, it may be determined that the femoral neck corresponding to the currently selected aperture in the body would position the femoral head at the wrong position in the inferior-superior direction as the gauge, when aligned with the linear indicium 122 is offset from the marking 424. Hence, the surgeon may select another one of the apertures, e.g. the aperture 116 and attach the gauge with its pin in that aperture with the arm of the gauge 144 aligned with the second linear indicium 124. The surgeon may then visually inspect the marking 424 to assess whether the corresponding femoral neck gives rise to a femoral head position sufficiently close in the inferior-superior and medial-lateral directions. If the arm 144 of the gauge is sufficiently close to the horizontal part of marking 424 and the vertical part of marking 424 corresponds to a sufficiently close separation in the medial-lateral axis, then the surgeon may select the corresponding femoral neck accordingly.

Hence, the plurality of apertures in the body 100 and the gauge 140 may be used to determine which of the plurality of femoral necks will give rise to a replacement femoral head with a centre most closely matching the centre of the native femoral head. This is achieved by providing a marking on the remaining part of the native femur 424 having a known positional relationship to the centre of the native femoral head. The gauge 144 and the apertures and linear indicia 122, 124 hence permit the surgeon to compare the resulting leg length and medial-lateral offset arising from the various femoral necks corresponding to the various apertures in the body.

Although the use of a scale and measuring specific distances is described above, it will be appreciated that this is not essential. Rather, the scale may simply use different markings indicating different amounts of separation. Absolute values of distance are not essential.

Also, as noted above, although the described embodiment uses five apertures each corresponding to a different femoral neck, a greater or lesser number of apertures of corresponding femoral necks may be used. Also, the specific geometries of the femoral necks described, in terms of their stem-neck angle and variations in leg length and medial-lateral offset are not essential.

Further, although a specific guide is illustrated in FIGS. 5 and 6 as being used to determine the approximate centre of the native femoral head, the use of such a guide is not essential. Any device that may be used to approximately identify the centre of the femoral head may be used. The identification of the preferred neck resection height and angle is merely incidental and is not essential in order to achieve the benefits of approximately restoring the centre of the femoral head.

In this specification, example embodiments have been presented in terms of a selected set of details. However, a person of ordinary skill in the art would understand that many other example embodiments may be practiced which include a different selected set of these details. It is intended that the following claims cover all possible example embodiments.

Any instructions and/or flowchart steps can be executed in any order, unless a specific order is explicitly stated. Also, those skilled in the art will recognize that while one example set of instructions/method has been discussed, the material in this specification can be combined in a variety of ways to yield other examples as well, and are to be understood within a context provided by this detailed description.

While the disclosure is amenable to various modifications and alternative forms, specifics thereof have been shown by way of example in the drawings and described in detail. It should be understood, however, that other embodiments, beyond the particular embodiments described, are possible as well. All modifications, equivalents, and alternative embodiments falling within the scope of the appended claims are covered as well.

The invention claimed is:

1. A surgical instrument for assessing restoration of the femoral head centre, comprising:
   a body having a first connector for attaching the body to a femoral part, and wherein (i) the body defines a plurality of apertures therein, wherein each aperture corresponds to a respective femoral head centre arising from a respective corresponding femoral neck, and (ii) the body has an anterior face and wherein the anterior face includes at least a first linear indicium extending parallel to a medial-lateral axis and passing through at least a first of the plurality of apertures and corresponding to a first position on a superior-inferior axis; and
   a gauge, wherein the gauge includes a pin at a first end and an arm extending transversely from the pin and wherein the pin is receivable in each of the plurality of apertures and the arm bears a scale indicating a distance from the pin.

2. The surgical instrument of claim 1, wherein the plurality of apertures includes apertures corresponding to femoral necks having different medial-lateral offsets.

3. The surgical instrument of claim 1, wherein the plurality of apertures includes apertures corresponding to femoral necks having different stem-neck angles.

4. The surgical instrument of claim 1, wherein the plurality of apertures includes apertures corresponding to femoral necks having different leg-lengths.

5. The surgical instrument of claim 1, wherein the anterior face includes at least a second linear indicium extending parallel to the medial-lateral axis and passing through at least a second of the plurality of apertures and corresponding to a second position on the superior-inferior axis.

6. The surgical instrument of claim 1, wherein the body has a posterior face and wherein the posterior face includes the same indicia as the anterior face and configured so that the same body is useable for right hand hips and left hand hips.

7. The surgical instrument of claim 1, wherein each of the plurality of apertures comprises a channel passing through the entire thickness of the body.

8. A surgical instrument system comprising:
   the surgical instrument of claim 1; and
   a centre finder, the centre finder including a plurality of indicia configured to indicate the centre of the centre finder, wherein the centre finder comprises a circular ring and wherein the plurality of indicia comprises a first pair of diametrically opposed indicia and a second pair of diametrically opposed indicia.

9. A surgical instrument system of claim 8 and further comprising:
   a broach, wherein the broach includes a second connector configured to engage the first connector to attach the body to the broach; and
   a plurality of femoral necks, wherein each neck gives rise to a different femoral head centre position.

10. The surgical instrument system of claim 9, wherein the plurality of femoral necks includes femoral necks having different offsets along the medial-lateral axis.

11. The surgical instrument system of claim 9, wherein the plurality of femoral necks includes femoral necks having different stem-neck angles.

12. The surgical instrument system of claim 9, wherein the plurality of femoral necks includes femoral necks having different leg lengths along the superior-inferior axis.

* * * * *